US006579841B1

(12) United States Patent
Day et al.

(10) Patent No.: US 6,579,841 B1
(45) Date of Patent: Jun. 17, 2003

(54) VARIANT EGIII-LIKE CELLULASE COMPOSITIONS

(75) Inventors: Anthony G. Day, San Francisco, CA (US); Peter Gualfetti, San Francisco, CA (US); Colin Mitchinson, Half Moon Bay, CA (US); Andrew Shaw, San Francisco, CA (US)

(73) Assignee: Genencor International, Inc., Palo Alto, CA (US)

( * ) Notice: Subject to any disclaimer, the term of this patent is extended or adjusted under 35 U.S.C. 154(b) by 240 days.

(21) Appl. No.: 09/633,085

(22) Filed: Aug. 4, 2000

Related U.S. Application Data

(63) Continuation-in-part of application No. 09/216,295, filed on Dec. 18, 1998, now Pat. No. 6,268,328.

(51) Int. Cl.$^7$ .......................... C11D 3/386; C12N 9/42; C12N 9/00
(52) U.S. Cl. ........................ 510/392; 510/392; 510/320; 510/321; 510/530; 510/226; 8/181; 8/137; 8/116.1; 435/209
(58) Field of Search ................................ 510/392, 320, 510/321, 530, 226; 8/181, 137; 435/209

(56) References Cited

U.S. PATENT DOCUMENTS

| | | | |
|---|---|---|---|
| 4,738,682 A | 4/1988 | Boegh et al. ................... 8/401 |
| 4,760,025 A | 7/1988 | Estell et al. ................ 435/222 |
| 4,832,864 A | 5/1989 | Olson .................... 252/174.12 |
| 5,185,258 A | 2/1993 | Caldwell et al. ............ 435/220 |
| 5,246,853 A | 9/1993 | Clarkson et al. ........... 435/203 |
| 5,254,283 A | 10/1993 | Arnold et al. ......... 252/174.12 |
| 5,290,474 A | 3/1994 | Clarkson et al. ....... 252/174.12 |
| 5,475,101 A | 12/1995 | Ward et al. ............... 536/23.74 |
| 5,798,327 A | 8/1998 | Casteleijn et al. .......... 510/303 |
| 5,877,139 A | 3/1999 | Casteleijn et al. .......... 510/303 |
| 5,919,691 A | 7/1999 | Schulein et al. ............ 435/209 |
| 6,001,639 A | 12/1999 | Schulein et al. ............ 435/263 |
| 6,268,328 B1 * | 7/2001 | Mitchinson et al. ........ 510/392 |

FOREIGN PATENT DOCUMENTS

| | | |
|---|---|---|
| EP | 220 016 | 8/1991 |
| EP | 271 004 | 4/1993 |
| EP | 0684 304 | 4/1995 |
| FI | 87372 | 9/1992 |
| GB | 2075028 | 4/1981 |
| GB | 1358599 | 7/1981 |
| GB | 2094826 | 3/1982 |
| GB | 2095275 | 3/1982 |
| WO | WO 91/04673 | 4/1991 |
| WO | WO 92/16687 | 10/1992 |
| WO | WO 93/20209 A | 10/1993 |
| WO | WO 94/14953 | 7/1994 |
| WO | WO 94/21801 A | 9/1994 |
| WO | WO 94/28117 | 12/1994 |
| WO | WO 95/16360 | 6/1995 |
| WO | WO 98/12307 A | 3/1998 |
| WO | WO 98/31821 | 7/1998 |
| WO | WO 99/31255 | 6/1999 |
| WO | WO 00/14206 | 3/2000 |
| WO | WO 00/14206 A | 3/2000 |
| WO | WO 00/14208 A | 3/2000 |
| WO | WO 00/14208 | 3/2000 |
| WO | WO 00/37614 | 6/2000 |
| WO | WO 01/47956 A2 | 7/2001 |
| WO | WO 02/12463 A2 | 2/2002 |
| WO | WO 02/12465 A2 | 2/2002 |

OTHER PUBLICATIONS

Altschul, S. et al., "Basic Local Alignment Search Tool" (1990) *J. Mol. Biol.* vol. 215, No. 3, pp. 403–410.

Ausubel F. et al. (1987) "Current Protocols in Molecular Biology," Greene Publ. And Wiley–Interscience, N.Y.

Bennett & Lasure (1991) "More Gene Manipulations in Fungi," Academic Press, San Diego, pp. 70–76.

Bergés, T. et al., "Isolation of uridine auxotrophs from *Trichoderma reesei* and efficient transformation with the cloned ura3 and ura5 genes" (1991) *Curr. Genet.* vol. 19, No. 5, pp. 359–365.

Berman et al., "The Protein Data Bank," *Nucleic Acids Research*, 2000, vol. 28, No. 1 pp. 235–242.

Gloss, L. et al., "Urea and ThermalEquilibrium Denaturation Studies on the Dimerization Domain of *Escherichia coli* Trp Repressor" (1997) *Biochem.* vol. 36, No. 19, pp. 5612–5623.

Henikoff & Henikoff, "Amino acid substitution matrices from protein blocks," (1989) *PNAS USA* 89:10915.

Karlin, S. et al., "Applications and statistics for multiple high–scoring segments in molecular sequences" (1993) *Proc. Natl. Acad. Sci. USA* vol. 90, No. 12, pp. 5873–5788.

Luo, J. et al., "Detection of a Stable Intermediate in the Thermal Unfolding of a Cysteine–Free Form of Dihydrofolate Reductase from *Escherichia coli*" (1995) *Biochem.* vol. 34, No. 33, pp. 10669–10675.

Mizobuchi et al., "Rapid Amplification of Genomic DNA Ends," (1993) *BioTechniques* 15:215–216.

Needleman, S. et al., "A General Method Applicable to the Search for Similarities in the Amino Acid Sequence of Two Proteins" (1970) *J. Mol. Biol.* vol. 48, pp. 443–453.

Pace, C. Nick, "How to measure and predict the molar absorption coefficient of a protein," Protein Science, Cambridge University Press, 4:2411–2423, 1995.

Pearson, W. et al., "Improved tools for biological sequence comparison" (1988) *Proc. Natl. Acad. Sci. USA* vol. 85, pp. 2444–2448.

Sambrook et al. (1989) Molecular Cloning: A Laboratory Manual, 2$^{nd}$ Ed., Cold Spring Harbor Press.

(List continued on next page.)

Primary Examiner—Yogendra N. Gupta
Assistant Examiner—Eisá Elhilo
(74) *Attorney, Agent, or Firm*—Genencor International, Inc.

(57) ABSTRACT

The present invention relates to novel variant EGIII or EGIII-like cellulases which have improved stability. The variant cellulases have performance sensitive residues replaced to a residue having modified stability.

21 Claims, 5 Drawing Sheets

OTHER PUBLICATIONS

Sandgren et al. (2001) "The X–ray Crystal Structure of the *Trichoderma reesei* Family 12 Endoglucanase 3, Cel12A, at 1.9 Å Resolution," *J. Mol. Biol.* (2001) 308, 295–310.

Sheir–Neiss, G., et al. "Characterization of the secreted cellulases of *Trichoderma reesei* wild type and mutants during controlled fermentations," Appl. Microbiol. Biotechnol., 20:46–53, 1984.

Smith, Temple F., et al., "Comparison of Biosequences," Adv. Appl. Math. 2:482–489, 1981.

Sulzenbacher, Gerlind, et al., "The *Streptomyces lividans* Family 12 Endoglucanase: Construction of the Catalytic Core, Exprssion, and X–ray Structure at 1.75 Å Resolution†‡," Biochemistry 36 :16032–16039, 1997.

Sulzenbacher, G. et al., "The Crystal Structure of a 2–Fluorocellotriosyl Complex of the *Streptomyces lividans* Endoglucanase CelB2 at 1.2 Å Resolution" (1999) *Biochem.* vol. 38, No. 15, pp. 4826–4833.

Hreggvidsson et al., "An Extremely Thermostable Cellulase from the Thermophilic Eubacterium *Rhodothermus marinus,*" Appl. *Environ. Microb.*, vol. 62, No. 8, pp. 3047–3049 (1996).

Knowles, J. et al., "Cellulase families and their genes," *TIBTECH* 5, 255–261, (1987).

Ooi et al., "Cloning and sequence analysis of a CDNA for cellulase (FI–CMCase) from *Aspergillus aculeatus,*" *Curr. Genet.*, vol. 18, pp. 217–222 (1990).

Saartilahti et al., "CeIS: a novel endoglucanase idenfitied from *Erwinia carotovora* subsp. *carotovora,*" *Gene*, vol. 90, pp. 9–14 (1990).

Sakamoto et al., "Cloning and sequencing of cellulase cDNA from *Aspergillus kawachii* and its expression in *Saccharomyces cerevisiae,*" Curr. *Genet.*, vol. 27 pp. 435–439 (1995).

Schulein et al., "[25] Cellulases of *Trichoderma reesei,*" *Methods in Enzymology*, 160, 25, pp. 234–242, (1988).

The Shizuoka Prefectural Hammamatsu Textile Industrial Research Institute Report, vol. 24, pp. 54–61 (1986)—listed but not provided.

Copy of PCT Search Report.

\* cited by examiner

Amino Acid Sequence of Mature EGIII Protein

```
QTSCDQWATFTGNGYTVSNNLWGASAGSGFGCVTAVSLSGGASWHADWQWSGGQNNVKSY   60
QNSQIAIPQKRTVNSISSMPTTASWSYSGSNIRANVAYDLFTAANPNHVTYSGDYELMIW  120
LGKYGDIGPIGSSQGTVNVGGQSWTLYYGYNGAMQVYSFVAQTNTTNYSGDVKNFFNYLR  180
DNKGYNAAGQYVLSYQFGTEPFTGSGTLNVASWTASIN            218
```

FIGURE 1

DNA Sequence of EGIII Without Introns

ATGAAGTTCCTTCAAGTCCTCCCTGCCCTCATACCGGCCGCCCTGG
CCCAAACCAGCTGTGACCAGTGGGCAACCTTCACTGGCAACGGCTA
CACAGTCAGCAACAACCTTTGGGGAGCATCAGCCGGCTCTGGATTT
GGCTGCGTGACGGCGGTATCGCTCAGCGGCGGGGCCTCCTGGCACG
CAGACTGGCAGTGGTCCGGCGGCCAGAACAACGTCAAGTCGTACC
AGAACTCTCAGATTGCCATTCCCCAGAAGAGGACCGTCAACAGCAT
CAGCAGCATGCCCACCACTGCCAGCTGGAGCTACAGCGGGAGCAA
CATCCGCGCTAATGTTGCGTATGACTTGTTCACCGCAGCCAACCCG
AATCATGTCACGTACTCGGGAGACTACGAACTCATGATCTGGCTTG
GCAAATACGGCGATATTGGGCCGATTGGGTCCTCACAGGGAACAG
TCAACGTCGGTGGCCAGAGCTGGACGCTCTACTATGGCTACAACGG
AGCCATGCAAGTCTATTCCTTTGTGGCCCAGACCAACACTACCAAC
TACAGCGGAGATGTCAAGAACTTCTTCAATTATCTCCGAGACAATA
AAGGATACAACGCTGCAGGCCAATATGTTCTTAGCTACCAATTTGG
TACCGAGCCCTTCACGGGCAGTGGAACTCTGAACGTCGCATCCTGG
ACCGCATCTATCAAC

FIGURE 2

```
                                     1                                                          60
                       T._reesei    M.........KF.LQVLPALIPAALAQTS...............CDQWATFTGNG..YTV
                  H._schweinitzii   M.........KF.LQVLPAILPAALAQTS...............CDQYATFSGNG..YIV
                    A._aculeatus *  M.........KAFHL.LAALAGAAVAQQAQ..............LCDQYATYTGGV..YTI
                    A._kawachii  *  M.........KLSMT.LSLFAATAMGQT................MCSQYDSASSPP..YSV
                    A._kawachii_2   M.........KAFHL.LAALSGAAVAQQAQ..............LCDQYATYTGGV..YTI
                    A._oryzae    *  M.........KLSLA.LATLVATAFSQE................LCAQYDSASSPP..YSV
                       H._grisei    M........LKSALLLGAAAVSVQSASIPTIPANLEPRQIR.SLCELYGYWSGNG..YEL
                    H._insolens  *  M........LKSALLLGPAAVSVQSASIPTIPANLEPRQIR.SLCELYGYWSGNG..YEL
             Chaetomium_brasiliense M.........KLTLVLFVSSLA......AATPLGWRERQQQVSLCGQSSSWSGNG..YQL
                       F._equseti   M.........KSTLLLAGAFAPLAFAKD................LCEQYGYLSSDG..YSL
                   F._javanicum_1   M.........KSAIVA.ALAGLAAASPTRLIPRGQ........FCGQWDSETAGA..YTI
                   F._javanicum_2   M.........K..FFGVVSASLAATAVATPTTPTETIEKRDTTWCDAFGSLATSG..YTV
                    G._roseum_Rj_1  M.........KANIVILSLFAPLAAVAQT...............LCGQYSSNTQGG..YIF
                    G._roseum_Rj_2  M.........KSIISFFGLATLVAAAPSQNPTRTQPLEKRATTLCGQWDSVETGG..YTI
                    G._roseum_PA_3  M.........KFQLLSLTAFAPLSLAA.................LCGQYQSQSQGG..YIF
                    G._roseum_Rj_4  M.........KTGIAYLAAVLPLA.MAES...............LCDQYAYLSRDG..YNF
                Memnoniella_echinata M.........KVAAL.LVALSPLAF.AQS...............LCDQYSYYSSNG..YEF
                 Emericella_desertoru M.........K..LLALSLVSLASAASAASIL.SNTFTRRSD.FCGQWDTATVGN..FIV
                 Actinomycete_11AG8   MRS......HPRS..ATM.TVLVVLASLGALLTAAAPAQANQQICDRYGTTTIQD.RYVV
                    S._lividans_CelB* MRTLRPQARAPRGLLAALGAVLAAFALVSSLVTAAAPAQADTTICEPFGTTTIQG.RYVV
              Rhodothermus_marinus * MNVMR..AVLVLSLLLLFGCDWL.FPDGDNGKEPEPEPEPTVELCGRWDARDVAGGRYRV
                    Erwinia_carot  * MQTVNTQPHRIFRVLLPAVFSSLLLSSLTVSAASSSNDADKLYF.........GNNKYYL 61                                                         120
                       T._reesei    SNNLWGASAGSGF..GCV.TAVSLSGG..ASWHADWQWSGGQNNVKSYQNS..........
                  H._schweinitzii   SNNLWGASAGSGF..GCV.TSVSLNGA..ASWHADWQWSGGQNNVKSYQNV..........
                    A._aculeatus *  NNNLWGKDAGSG..SQCTTVNSASSAG.TSWSTKWNWSGGENSVKSYANS..........
                    A._kawachii  *  NQNLWGEYQGTG..SQCVYVDKLSSSG.ASWHTKWTWSGGEGTVKSYSNS..........
                    A._kawachii_2   NNNLWGKDAGSG..SQCTTVNSASSAG.TSWSTKWNWSGGENSVKSYANS..........
                    A._oryzae    *  NNNLWGQDSGTGFTSQCVYVDNLSSSG.AAWHTTWTWNGGEGSVKSYSNS..........
                       H._grisei    LNNLWGKDTATS.GWQCTYLDGTNNGG.IQWSTAWEWQGAPDNVKSYPYV..........
                    H._insolens  *  LNNLWGKDTATS.GWQCTYLDGTNNGG.IQWSTAWEWQGAPDNVKSYPYV..........
             Chaetomium_brasiliense NNNLWGQSRATS.GSQCTYLDSSSNSG.IHWHTTWTWEGGEGEVKSYAYS..........
                       F._equseti   NNNVWGKDSGTGD..QCTHVNWNNANG.AGWDVEWNWSGGKDNVKSYPNS..........
                   F._javanicum_1   YNNLWGKDNAES.GEQCTTNSGEQSDGSIAWSVEWSWTGGQGQVKSYPNA..........
                   F._javanicum_2   YHNNWGKGDATS.GSQCTTFTSVSNNNFV.WSTSWTWAGGAGKVKSYSNV..........
                    G._roseum_Rj_1  NNNMWGMGSGSGS..QCTYVDKVWAEG.VAWHTDWSWSGGDNNVKSYPYS..........
                    G._roseum_Rj_2  YNNLWGQDNG.S.GSQCLTVEGV.TDGLAAWSSTWSWSGGSSSVKSYSNA..........
                    G._roseum_PA_3  NNNKWGQGSGSGS..QCLTIDKTWDSN.VAFHADWSWSGGTNNVKSYPNA..........
                    G._roseum_Rj_4  NNNEWGAATGTGD..QCTYVDSTSSGG.VSWHSDWTWSGSESESEIKSYPYS..........
                Memnoniella_echinata NNNMWGRNSGQGN..QCTYVDYSSPNG.VGWRVNWNWSGGDNNVKSYPYS..........
                 Emericella_desertoru YNNLWGQDNADS.GSQ..TGVDSANGNSISWHTTWSWSGGSSSVKSYANA..........
                 Actinomycete_11AG8  QNNRWGTSAT.....QCINVT..GNGFEITQADGS..VPTNGAPKSYPSVYDGCHYG...
                    S._lividans_CelB* QNNRWGSTAP.....QCVTAT..DTGFRVTQADGS...APTNGAPKSYPSVFNGCHYT...
              Rhodothermus_marinus * INNVWGAETA.....QCIEVGLETGNFTITRADHD..NGNNVA..AYPAIYFGCHWAPAR
                    Erwinia_carot  * FNNVWGKDEIKGWQQTIFYNSPISMG....WN..WHWPSSTHSVKAYPSLVSGWHWTAG.

121                                                        180
                       T._reesei    .QIAIP.QKRTVNSISSMPTTASW...SYSGSNIRANVAYDL.FTAANPNHVTYSGDYEL
                  H._schweinitzii   .QINIP.QKRTVNSIGSMPTTASW...SYSGSDIRANVAYDL.FTAANPNHVTYSGDYEL
                    A._aculeatus *  .GLTF..NKKLVSQISQIPTTARW.S..YDNTGIRADVAYDL.FTAADINHVTWSGDYEL
                    A._kawachii  *  .GLTF..DKKLVSDVSSIPTSVTW.SQD..DTNVQADVSYDL.FTAANADHATSSGDYEL
                    A._kawachii_2   .GLSF..NKKLVSQISHIPTAARW.S..YDNTCIRRGRAYDL.FTAADINHVTYSGDYEL
                    A._oryzae    *  .AVTF..DKKLVSDVQSIPTDVEW.SQD.FTNTNVNADVAYDL.FTAADQNHVTYSGDYEL
                       H._grisei    .GKQIQRGRK.ISDINSMRTSVSW...TYDRTDIRANVAYDV.FTARDPDHPNWGGDYEL
                    H._insolens  *  .GKQIQRGRK.ISDINSMRTSVSW...TYDRTDIRANVAYDV.FTARDPDHPNWGGDYEL
             Chaetomium_brasiliense .GRQVSTGLT.IASIDSMQTSVSW...EYNTTDIQANVAYDI.FTAEDPDHEHSSGDYEL
                       F._equseti   .ALLIGEDKKTISSITNMQSTAEW...KYSGDNLRADVAYDL.FTAADPNHETSSGEYEL
                   F._javanicum_1   .VVEI..EKKTLGEVSSIPSA..W.DWTYTGNGIIANVAYDL.FTSSTESGDA...EYEF
                   F._javanicum_2   .ALEK..INKKISDIKSVSTR..W.IWRYTGTKMIANVSYDL.WFAPTASSNN...AYEI
                    G._roseum_Rj_1  .GRELGT.KRIVSSIKSISSGADW...DYTGSNLRANAAYDI.FTSANPNHATSSGDYEV
                    G._roseum_Rj_2  .VLSA..EAARISAISSIPSK..W.EWSYTGTDIVANVAYDL.FSNTDCGDTP...EYEI
                    G._roseum_PA_3  .GLEFSR.GKKVSSIGTINGGADW...DYSGSNIRANVAYDI.FTSADPNHVTSSGDYEL
                    G._roseum_Rj_4  .GLDLPE.KKIVTSIGSISTGAEW...SYSGSDIRADVAYDT.FTAADPNHATSSGDYEV
                Memnoniella_echinata .GRQLPT.KRIVSWIGSLPTTVSW...NYQGNNLRANVAYDL.FTAANPNHPNSSGDYEL
                 Emericella_desertoru .AYQF..TSTKLNSLSSIPTS..W.KWQYSTTDIVANVAYDL.FTSSSAGGDS...EYEI
```

FIGURE 3A

```
    Actinomycete_11AG8  ...NCAPRTTLPMRISSIGSAPSSVSYRYTGNGVY.NAAYDIWLDPTPRTNGVNR..TEI
      S._lividans_CelB_*  ...NCSPGTDLPVRLDTVSAAPSSISYGFVDGAVY.NASYDIWLDPTARTDGVNQ..TEI
Rhodothermus_marinus__*  AIRDCAARAGAVRRAHELDVTP.......ITTGRW.NAAYDIWFSPVTNSGNGYSGGAEL
       Erwinia_carot___*  ....YTENSGLPIQLSSNKSITSNVTYSIKATGTY.NAAYDIWFHTTDKANWDSSPTDEL 181                                                      240
              T._reesei  MIWLGKYGDIGPIGSS....QGTVNVGGQSWTLYYGYNGAMQV......YSFVAQT.NTT
         H._schweinitzii  MIWLGKYGDIGPIGSS....QGTVNVGGQTWTLYYGYNGAMQV......YSFVAQS.NTT
            A._aculeatus_*  MIWLARYGGVQPIGSQ....IATATVDGQTWELWYG......ANGSQKTYSFVAPT.PIT
             A._kawachii_*  MIWLARYGSVQPIGKQ....IATATVGGKSWEVW..YGTSTQAGAEQKTYSFVAGS.PIN
             A._kawachii_2  MIWLARYGGVQPLGSQ....IATATVEGQTWELWYG......VNGAQKTYSFVAAN.PIT
              A._oryzae__*  MIWLARYGTIQPIGTQ....IDTATVEGHTWELWFTYGTTIQAGAEQKTYSFVSAT.PIN
               H._grisei  MIWLARYGGIYPIGTF....HSQVNLAGRTWDLWTGYNGNMRV......YSFLPPSGDIR
             H._insolens_*  MIWLARYGGIYPIGTF....HSQVNLAGRTWDLWTGYNGNMRV......YSFLPPSGDIR
    Chaetomium_brasiliense  MIWLARYNNVSPIGSS....VATATVGGDTWDLFAGANGDMEV......YSFVAENT.MN
              F._equseti  MVWLARIGGVQPIGSL....QTSVTIEGHTWELWVGMNGSMKV......FSFVAPT.PVN
            F._javanicum_1  MIWLSALGGAGPISNDGSP.VATAELAGTSWKLYQGKNNQMTV......FSFVAESDV.N
            F._javanicum_2  MIWVGAYGGALPISTPGKGVIDRPTLAGIPWDVYKGPNGDVTV......ISFVASSNQ.G
             G._roseum_Rj_1  MIWLANLGGLTPIGSP....IGTVKAAGRDWELWDGYNGAMRV......YSFVAPS.QLN
             G._roseum_Rj_2  MIWLSALGGAGPISSTGSS.IATVTIAGASWNLWQGQNNQMAV......FSFVAESDQ.K
             G._roseum_PA_3  MIWLGKLGDIYPIGNS....IGRVKAANREWDLHVGYNGAMKV......FSFVAPS.PVT
             G._roseum_Rj_4  MIWLANLGGLTPIGSP....IGTVKAAGRDWELWDGYNGAMRV......YSFVAPS.QLN
       Memnoniella_echinata  MIWLGRLGNVYPIGNQ....VATVNIAGQQWNLYYGYNGAMQV......YSFVSPN.QLN
       Emericella_desertoru  MIWLAALGGAGPISSTGSS.IATVTLGGVTWSLYSGPNGSMQV......YSFVASSTT.E
    Actinomycete_11AG8  MIWFNRVGPVQPIGSP....VGTAHVGGRSWEVWTGSNGSNDVI......SFLAPSA.IS
      S._lividans_CelB_*  MIWFNRVGPIQPIGSP....VGTASVGGRTWEVWSGGNGSNDVL......SFVAPSA.IS
Rhodothermus_marinus__*  MIWLNWNGGVMPGGSR....VATVELAGATWEVWYADWDWNYIA......YRRTTPT.TS
       Erwinia_carot___*  MIWLNDTNA.....GPAGDYIETVFLGDSSWNVFKGWINADN.GGGWNVFSFVHTSGTNS 241                                                      300
              T._reesei  NYSGDVKNFFNYLRDNKGYNAAGQYV..LSYQFGTEPF..TGSGT.LNVASWTASI.N..
         H._schweinitzii  SYSGDVKNFFNYLRDNKGYNAGGQYV..LSYQFGTEPF..TGSGT.LNVASWTASI.N..
            A._aculeatus_*  SFQGDVNDFFKYLTQNHGFPASSQYLI..TLQFGTEPF..TGGPATLSVSNWSASVQQAG
             A._kawachii_*  SWSGDIKDFFNYLTQNQGFPASSQHLI..TLQCGTEPF..TGGPATFTVDNWTASVN...
             A._kawachii_2  SFQGDINDFFKYLTQNHGFPASSQYLIILALQFGTEPF..TGGPATLNVADWSASVQ...
              A._oryzae__*  TFGGDIKKFFDYITSKHSFPASAQYLI..NMQFGTEPFFTTGGPVTFTVPNWTASVN...
               H._grisei  DFSCDIKDFFNYLERNHGYPAREQNLIV..YQVGTECF..TGGPARFTCRDFRADL....
             H._insolens_*  DFSCDIKDFFNYLERNHGYPAREQNLIV..YQVGTECF..TGGPARFTCRDFRADL....
    Chaetomium_brasiliense  SFSGDVKDFFDYLEQNVGFPVDDQYLLV..FELGSEAF..TGGPATLSVSQFSANI....
              F._equseti  NFNADIKQFWDYLTKSQNFPADNQYL..LTFQFGSTEPF..TGDNAKFTVTNFNAHLK...
            F._javanicum_1  NFCGDLADFTDYLVDNHGVSSSQ...ILQSVGAGTEPF..EGTNAVFTTNNYHADVE...
            F._javanicum_2  NFQADLKEFLNYLTSKQGLPSNY...VATSFQAGTEPF..EGTNAVLKTSAYTISVN...
             G._roseum_Rj_1  SFDGEIMDFFYVVKDMRGFPADSQHL..LTVQFGTEPI..SGSGAKFSVSHWSAKLG...
             G._roseum_Rj_2  SFSGDLNDFIQYLVDSQGYSGSQ...CLYSIGAGTEPF..TGTDAEFITTGYSVSVSAGD
             G._roseum_PA_3  RFDGNIMDFFYVMRDMQGYPMDKQYL..LSLQFGTEPF..TGSNAKFSCWYFGAKIK...
             G._roseum_Rj_4  SFDGEIMDFFYVVKDMRGFPADSQHL..LTVQFGTEPI..SGSGAKFSVSHWSAKLG...
       Memnoniella_echinata  YFSGNVKDFFTYLQYNRAYPADSQYL..ITYQFGTEPF..TGQNAVFTVSNWSAQQNN..
       Emericella_desertoru  SFSADLMDFINYLAENQGLSSSQ...YLTHVQAGTEPF..TGTDATLTVSSYSVSVS...
    Actinomycete_11AG8  SWSFDVKDFVD.QAVSHGLATPDWYLT..SIQAGFEPW...EGGTGLAVNSFSSAVNAG.
      S._lividans_CelB_*  GWSFDVMDFVR.ATVARGLAENDWYLT..SVQAGFEPW...QNGAGLAVNSFSSTVETGT
Rhodothermus_marinus__*  VSELDLKAFID.DAVARGYIRPEWYLH..AVETGFELW...EGGAGLRTADFSVTVQ...
       Erwinia_carot___*  A.SLNIRHFTDYLVQTKQWMSDEKYIS..SVEFGTEIF...GGDGQIDITEWRVDVK...

301                                                      360
              T._reesei  ..........................................................
         H._schweinitzii  ..........................................................
            A._aculeatus_*  F.........................................EPWQNGAGLAVNSF....
             A._kawachii_*  ..........................................................
             A._kawachii_2  ..........................................................
              A._oryzae__*  ..........................................................
               H._grisei  ........................................W.................
             H._insolens_*  ........................................W.................
    Chaetomium_brasiliense  ........................................A.................
              F._equseti  ..........................................................
            F._javanicum_1  ..........................................................
            F._javanicum_2  ..........................................................
             G._roseum_Rj_1  ..........................................................
             G._roseum_Rj_2  SGCDETTTSSQAQSSTVETSTATQPQS...SSTVVPTVTLS.QPSNESTTTPVQSQ....
             G._roseum_PA_3  ..........................................................
             G._roseum_Rj_4  ..........................................................
       Memnoniella_echinata  ..........................................................
       Emericella_desertoru  ..........................................................
    Actinomycete_11AG8  ..GGNGGTPGTPAACQVSYSTHTWPGGFTVDTTITNTGSTPVDGWELDFTLPAGHTVTSA
      S._lividans_CelB_*  PGGTDPGDPGGPSACAVSYGTNVWQDGFTADVTVTNTGTAPVDGWQLAFTLPSGQRITNA
Rhodothermus_marinus__*  ..........................................................
```

FIGURE 3B

```
                Erwinia_carot___*    .................................................
                                    361
         419
  5              T._reesei          .................................................
             H._schweinitzii        .................................................
              A._aculeatus_*        ......SSTV.......................................
               A._kawachii_*        .................................................
               A._kawachii_2        .................................................
 10             A._oryzae__*        .................................................
                 H._grisei          .................................................
              H._insolens__*        .................................................
       Chaetomium_brasiliense       .................................................
                F._equseti          .................................................
 15           F._javanicum_1        ................................................Y
              F._javanicum_2        .................................................
              G._roseum_Rj_1        .................................................
              G._roseum_Rj_2        ......PSSVETTPTAQPQSSSVQTTTTAQA....QPTSGTGCSRRRKRR......AVV
              G._roseum_PA_3        .................................................
 20           G._roseum_Rj_4        .................................................
         Memnoniella_echinata       .................................................
         Emericella_desertoru       .................................................
            Actinomycete_11AG8      WNALISPASGAVTARSTGSNGRIAANGGTQSFGFQGTSSGTGFNAPAGGRLNGTSCTVR
              S._lividans_CelB_*    WNASLTPSSGSVTATGASHNARIAP.GGSLSFGFQGTYGGA.FAEPTGFRLNGTACTTV
 25      Rhodothermus_marinus__*    .................................................
                Erwinia_carot___*   .................................................
```

FIGURE 3C

VARIANT EGIII-LIKE CELLULASE COMPOSITIONS

CROSS-REFERENCE TO RELATED APPLICATIONS

This application is a Continuation-in-Part of U.S. Ser. No. 09/216,295, filed Dec. 18, 1998 now U.S. Pat. No. 6,268,328 B1, which is incorporated by reference in its entirety. This application is related to concurrently filed applications with attorney docket numbers GC629, GC546C1, GC630, and GC631, all of which were filed on Aug. 4, 2000 and are incorporated by reference in their entirety.

GOVERNMENT-SPONSORED RESEARCH AND DEVELOPMENT

Not applicable.

BACKGROUND OF THE INVENTION

Cellulases are enzymes that are capable of hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al., (1987), TIBTECH 5, 255–261); and are known to be produced by a large number of bacteria, yeasts and fungi.

Although cellulases are used to degrade wood pulp and animal feed, cellulases are primarily used in the treatment of textiles, e.g., in detergent compositions for assisting in the removal of dirt or grayish cast (see e.g., Great Britain compositions for assisting in the removal of dirt or grayish cast (see e.g., Great Britain Application Nos. 2,075,028, 2,095,275 and 2,094,826) or in the treatment of textiles prior to sale to improve the feel and appearance of the textile. Thus, Great Britain Application No. 1,358,599 illustrates the use of cellulase in detergents to reduce the harshness of cotton containing fabrics.

Cellulases have also been used in the treatment of textiles to recondition used fabrics by making their colors more vibrant (see e.g., The Shizuoka Prefectural Hammamatsu Textile Industrial Research Institute Report, Vol. 24, pp. 54–61 (1986)). Repeated washing of cotton containing fabrics results in a grayish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Because of its effectiveness in many industrial processes, there has been a trend in the field to search for specific cellulase compositions or components that have particularly effective performance profiles with respect to one or more specific applications. As possible sources of cellulases, practitioners have focused on fungi and bacteria. For example, cellulase produced by certain fungi such as Trichoderma spp. (especially Trichoderma reesei) have been given much attention because a complete cellulase system capable of degrading crystalline forms of cellulose is readily produced in large quantities via fermentation procedures. This specific cellulase complex has been extensively analyzed to determine the nature of its specific components and the ability of those components to perform in industrial processes (see, Wood et al., "Methods in Enzymology", 160, 25, pages 234, et seq. (1988). U.S. Pat. No. 5,475,101 (Ward et al.) discloses the purification and molecular cloning of one particularly useful enzyme called endoglucanase III (EGIII) which is derived from Trichoderma reesei.

PCT Publication No. WO 94/14953 discloses endoglucanases that are encoded by a nucleic acid which comprises any one of a series of DNA sequences, each having 20 nucleotides.

Ooi, et al., Curr. Genet. 18:217–222 (1990) disclose the cDNA sequence coding for endoglucanase F1-CMC produced by Aspergillus aculeatus that contains the amino acid strings NNLWG, ELMIW and GTEPFT. Sakamoto, et al., Curr. Genet. 27:435–439 (1995) discloses the cDNA sequence encoding the endoglucanase CMCase-1 From Aspergillus kawachii IFO 4308 which contains the amino acid strings ELMIW and GTEPFT. Ward, et al., discloses the sequence of EGIII having the amino acid strings NNLWG, ELMIW and GTEPFT. Additionally, two cellulase sequences, one from Erwinia carotovara and Rhodothermus marinus are disclosed in Saarilahti, et al., Gene 90:9–14 (1990) and Hreggvidsson, et al., Appl. Environ. Microb. 62:3047–3049 (1996) that contain the amino acid string ELMIW.

Despite knowledge in the art related to many cellulase compositions having applications in some or all of the above areas, there is a continued need for new cellulase compositions which have improved stability under conditions present in applications for which cellulases are useful, e.g., household and laundry detergents and textile treatment compositions.

SUMMARY OF THE INVENTION

A variant EGIII or EGIII-like cellulase is provided, wherein the variant comprises a substitution or deletion at a position corresponding to one or more of residues W7, G31, A35, T145, Y147, Q162 and/or Y168 in EGIII from Trichoderma reesei. In a preferred embodiment, the variant comprises a substitution at a position corresponding to one or more of residues W7Y, G31Q, A35V, T145E, Y147W, Q162P, and/or Y168F in EGIII. In one aspect of this embodiment, the cellulase is derived from a fungus, bacteria or Actinomycete. In a more preferred aspect, the cellulase is derived from a fungus. In a most preferred embodiment, the fungus is a filamentous fungus. It is preferred the filamentous fungus belong to Euascomycete, in particular, Aspergillus spp., Gliocladium spp., Fusarium spp., Acremonium spp., Myceliophtora spp., Verticillium spp., Myrothecium spp., or Penicillium spp. In another aspect of this embodiment, the cellululase is an endoglucanase.

In another embodiment of the invention, a DNA that encodes an EGIII variant is provided. In a preferred embodiment, the DNA is in a vector. In a further embodiment, the vector is used to transform a host cell.

In another embodiment of this invention, a method for producing an EGIII variant cellulase is provided. The method comprises the steps of culturing the host cell according to claim 11 in a suitable culture medium under suitable conditions to produce cellulase and obtaining the produced cellulase.

In yet another embodiment of the invention, a detergent comprising a surfactant and a cellulase is provided. In preferred embodiments, the cellulase comprises a variant EGIII-like cellulase comprising a substitution or deletion at a position corresponding to one or more of residues W7, G31, A35, T145, Y147, Q162 and/or Y168 in EGIII from Trichoderma reesei. In a more preferred embodiment, the cellulase comprises a substitution at a position corresponding to one or more of residues residues W7Y, G31Q, A35V, T145E, Y147W, Q162P, and/or Y168F in EGIII.

In a preferred aspect of this invention, the detergent is a laundry or a dish detergent. In another embodiment of this invention, the variant EGIII or EGIII-like cellulase is used in the treatment of a cellulose containing textile, in particular, in the stonewashing or indigo dyed denim. Alternatively, the cellulase of this invention can be used as a feed additive, in the treatment of wood pulp, and in the reduction of biomass to glucose.

BRIEF DESCRIPTION OF THE DRAWINGS

FIG. 1 illustrates the amino acid sequence of mature EGIII protein from *Trichoderma reesei* showing the residues described in accordance with the present invention.

FIG. 2 illustrates the DNA sequence of EGIII from *Trichoderma reesei* without introns.

FIG. 3 illustrates an alignment of the fill length sequence of 20 EGIII-like cellulases in alignment with EGIII, indicating equivalent residues based on primary sequence modeling, including those derived from *Trichoderma reesei, Hypocrea schweinitzii, Aspergillus aculeatus, Aspergillus kawachii* (1), *Aspergillus kawachii* (2), *Aspergillus oryzae, Humicola grisea, Humicola insolens, Chaetomium brasilliense, Fusarium equiseti, Fusarium javanicum* (1), *Fusarium javanicum* (2), *Gliocladium roseum* (1), *Gliocladium roseum* (2), *Gliocladium roseum* (3), *Gliocladium roseum* (4), *Memnoniella echinata, Emericella desertoru*, Actinomycete 11AG8, *Streptomyces lividans* CelB, *Rhodothermus marinus*, and *Erwinia carotovara*.

DETAILED DESCRIPTION OF THE INVENTION

Applicants have isolated novel members of a family of cellulases that have homology to EGIII from *Trichoderma reesei*. Analysis of these cellulases has resulted in differential performance between the cellulases, despite significant homology. In particular, it was discovered that the EGIII-like cellulases from *Humicola insolens, Humicola grisea, Memnonella echinata, Fusarium javanicum* and *Emericella desertoru* have superior performance under conditions of thermal stress. By aligning the amino acid sequences in these EGIII-like cellulases with that of EGIII, it is possible to identify residue differences between the thermally more stable cellulases and EGIII, thus identifying residues which are important for the improved thermal stability of EGIII-like cellulases. Accordingly, by optimizing the identified residues in EGIII as well as in the EGIII-like cellulases, it is possible to further improve the thermal stability of both the EGIII and the EGIII-like cellulases.

The present invention thus encompasses all such modifications that are identified through the amino acid sequence comparison of EGIII-like cellulases. Particular attention is made to those modifications that result in a change of enzyme thermal stability.

The improved protein according to the present invention comprises an amino acid sequence that is derived from the amino acid sequence of a precursor protein. The precursor protein may be a naturally occurring protein or a recombinant protein. The amino acid sequence of the improved protein is derived from the precursor protein's amino acid sequence by the substitution, deletion or insertion of one or more amino acids of the precursor amino acid sequence. Such modification is generally of the precursor DNA sequence that encodes the amino acid sequence of the precursor proteins rather than manipulation of the precursor protein per se. Suitable methods for such manipulation of the precursor DNA sequence include methods disclosed herein and in commonly owned U.S. Pat. Nos. 4,760,025 and 5,185,258, incorporated herein by reference.

Sequence alignments may be produced using different EGIII-like cellulases and may slightly differ from one alignment to another depending on the number of sequences and the degree of homology. Suitable experiments to determine appropriate modifications are routine to the ordinarily skilled worker in conjunction with the present disclosure.

Within the specification, certain terms are disclosed which are defined below so as to clarify the nature of the claimed invention.

"Cellulase" is a well-classified category of enzymes in the art and includes enzymes capable of hydrolyzing cellulose polymers to shorter cellooligosaccharide oligomers, cellobiose and/or glucose. Common examples of cellulase enzymes include exo-cellobiohydrolases and endoglucanases and are obtainable from many species of cellulolytic organisms, particularly including fungi and bacteria.

"EGIII" cellulase refers to the endoglucanase component described in Ward et al., U.S. Pat. No. 5,475,101 and Proceedings on the Second TRICEL Symposium on *Trichoderma reesei* Cellulases And Other Hydrolases, Suominen & Reinikainen eds., Espoo Finland (1993), pp. 153–158 (Foundation for Biotechnical and Industrial Fermentation Research, Vol. 8). As discussed therein, EGIII is derived from *Trichoderma reesei* and is characterized by a pH optimum of about 5.8, an isoelectric point (pI) of about 7.4 and a molecular weight of about 25 kD. The enzyme commonly referred to as EGII from *Trichoderma reesei* has been previously referred to in the literature by the nomenclature EGIII by some authors, but that enzyme differs substantially from the enzyme defined herein as EGIII in terms of molecular weight, pI and pH optimum.

"EG-III like enzyme", "EGIII-like protein" or "EGIII-like cellulase" according to the present invention means enzymes that are related to EGIII by having certain amino acid strings in common with EGIII. As used herein, EGIII-like cellulase is also intended to encompass EGIII from *Trichoderma reesei*. Thus an EGIII-like cellulase comprises an enzyme having cellulolytic activity which comprises an amino acid sequence comprising therein an amino acid string selected from the group consisting of one or more of:

1) Asn-Asn-(Leu/Phe/Lys/Ile)-Trp-Gly
2) Glu-(Leu/Phe/Ile)-Met-Ile-Trp
3) Gly-Thr-Glu-Pro-Phe-Thr;
4) (Ser/Tyr/Cys/Trp/Thr/Asn/Lys/Arg)-(Val/Pro)-(Lys/Ala)-(Ser/Ala)-(Tyr/Phe); and
5) Lys-Asn-Phe-Phe-Asn-Tyr.

In one embodiment, the enzyme of the invention further has significant structural and/or sequence homology to EGIII. Thus, in one aspect of this embodiment of the invention, the enzyme has at least 30%, preferably at least 40% and most preferably at least 60% amino acid identity to EGIII. However, it should be recognized that homology alone is often not an appropriate measure for whether a particular enzyme identified by the methods described herein represents an EGIII-like enzyme. Similar enzymatic function with or without reduced homology may identify an EGIII-like cellulase. Accordingly, while homologous enzymes are indeed detected by the methods described and exemplified herein, the degree of homology should not be seen as limiting the scope of the invention.

It is contemplated the EGIII-like cellulases of the invention may be found in many organisms which produce cellulases. However, likely sources of EGIII-like cellulase include those derived from a bacterium or fungus, and more particularly, from an Actinomycete, a Bacillus or a filamentous fungus. In a preferred embodiment, the cellulase is derived from the filamentous fungal family Metazoa, preferably Euascomycetes. Within Metazoa, fungal phylogenetic classifications that produce EGIII-like cellulases include the mitosporic Pyrenomycetes (including Acremonium), Sordariales (including Thielavia), Hypocreales (including Nectriaceae such as Fusariun, Necitia, Verticillium, Myrothecium and Gliocladium; and Hypocrea) and Eurotiales (including mitosporic Trichocomaceae such as Aspergillus and Penicillium).

The Euascomycete preferably belongs to Diaporthales, Halosphaeriales, Microascales, Ophiostomatales, Phyllachorales, Sordariales or Xylariales. Also preferably, the Eusacomycete belongs to Hypocreales comprising Clavicipitaceae, Melanosporaceae, Nectriaceae, Niessliaceae or Mitosporic Hypocreales. Further preferably, the Euascomycete belongs to Hypocreaceae, wherein said Hypocreaceae does not comprise Trichoderma. Most preferably, the Euascomycete is Gliocladium spp., Fusarium spp., Acremonium spp., Myceliophtora spp., Verticillium spp., Myrothecium spp., Penicillium spp., Chaetomium spp., Emercella spp., and Phanerochaete spp. Specific organisms which are contemplated as possessing EGIII-like cellulases include *Chaetomium thermophilum* var. *therm.*, *Chaetomium atrobrunneum*, *Chaetomium brasiliense*, *Chaetomium globosum*, *Chaetomium vitellium*, *Paecilomyces lilacinus*, *Chaetomium thermophilum* var. *dissitum*, *Humicola insolens*, *Humicola brevis*, *Memnoniella echinata*, *Fusarium equiseti*, *Fusarium oxysporum*, *fusarium stilboides*, *Myceliophthora thermophila*, *Fusarium javanicum*, *Humicola grisea* var. *thermoidea*, *Stibella thermophila*, *Melanocarpus albomyces*, *Arthrobotrys superba*, *Myceliophthora hinunilea*, *Chaetomium pachypodiodes*, *Myrothecium verrucaria*, *Penicillium crysogenum*, *Malbranchea sulfurea*, *Lunulospora curvula*, *Emericella desertorum*, *Acremonium strictum*, *Cylindrocarpon heteronema*, and *Ulocladium chartarum*. Within the Actinomycetes, Streptomyces appears to possess EGIII-like cellulases.

EGII-like cellulases according to the invention may be obtained according to the following methods. Degenerate DNA primers are constructed which encode an amino acid sequence selected from the group consisting of one or more of:

1) Asn-Asn-(Leu/Phe/Lys/Ile)-Trp-Gly
2) Glu-(Leu/Phe/Ile)-Met-Ile-Trp
3) Gly-Thr-Glu-Pro-Phe-Thr;
4) (Ser/Tyr/Cys/Trp/Thr/Asn/Lys/Arg)-(Val/Pro)-(Lys/Ala)-(Ser/Ala)-(Tyr/Phe); and
5) Lys-Asn-Phe-Phe-Asn-Tyr and used to clone DNA, and genes, encoding enzymes having cellulolytic activity according to established methods. Techniques for obtaining DNA using degenerate primers are well known in the art and can be found in Sambrook et al. Molecular Cloning—A Laboratory Manual (2ND ED.) VOL. 1–3, Cold Springs Harbor Publishing (1989) ("Sambrook"); and Current Protocols in Molecular Biology, Ausubel et al. (eds.), Current Protocols, a joint venture between Greene Publishing Associates, Inc. and John Wiley & Sons, Inc., (1997 Supplement) ("Ausubel"). In addition, the EGIII of the invention may be obtained by other methods conventional in molecular biology, e.g., library screening with labeled probes, expression screening and PCR cloning, using one of the cellulase backbones identified herein as an EGIII-like cellulase.

The degenerate primers can be used as hybridization probes against a genomic library obtained from a target organism to analyze whether a given fragment correlates to a similar sequence in the target organism. A useful hybridization assay is as follows: Genomic DNA from a particular target source is fragmented by digestion with a restriction enzyme(s), e.g., EcoR I, Hind III, Bam HI, Cla I, Kpn I, Mlu I, Spe I, Bgl II, Nco I, Xba I, Xho I and Xma I (supplied by New England Biolabs, Inc., Beverly, Mass. and Boehringer Mannheim) according to the manufacturer's instructions. The samples are then electrophoresed through an agarose gel (such as, for example, 0.7% agarose) so that separation of DNA fragments can be visualized by size. The gel may be briefly rinsed in distilled $H_2O$ and subsequently depurinated in an appropriate solution (such as, for example, 0.25M HCl) with gentle shaking followed by denaturation for 30 minutes (in, for example, 0.4 M NaOH). A renaturation step may be included in which the gel is placed in 1.5 M NaCl, IM Tris, pH 7.0 with gentle shaking for 30 minutes. The DNA is then be transferred onto an appropriate positively charged membrane, for example the Maximum Strength Nytran Plus membrane (Schleicher & Schuell, Keene, N.H.), using a transfer solution (such as, for example, 6×SSC (900 mM NaCl, 90 mM trisodium citrate). After the transfer is complete, generally at about 2 hours or greater, the membrane is rinsed (in, for example, 2×SSC[2×SSC=300 mM NaCl, 30 mM trisodium citrate]) and air dried at room temperature. The membrane is then be prehybridized, (for approximately 2 hours or more) in a suitable prehybridization solution (such as, for example, an aqueous solution containing per 100 mL: 30–50 mL formamide, 25 mL of 20×SSPE (1×SSPE=0.18 M NaCl, 1 mM EDTA, 10 mM $NaH_2PO_4$, pH 7.7), 2.5 mL of 20% SDS, and 1 mL of 10 mg/ml sheared herring sperm DNA).

A DNA probe, corresponding to the primer sequences above, is isolated by electrophoresis in an agarose gel, the fragment excised from the gel and recovered from the excised agarose. This purified fragment of DNA is then labeled (using, for example, the Megaprime labeling system according to the instructions of the manufacturer to incorporate $P^{32}$ in the DNA (Amersham International PLC, Buckinghamshire, England)). The labeled probe is denatured by heating to 95° C. for 5 minutes and immediately added to the prehybridization solution above containing the membrane. The hybridization reaction should proceed for an appropriate time and under appropriate conditions, for example, 18 hours at 37° C. with gentle shaking. The membrane is rinsed (for example, in 2×SSC/0.3% SDS) and then washed with an appropriate wash solution and with gentle agitation. The stringency desired will be a reflection of the conditions under which the membrane (filter) is washed.

Specifically, the stringency of a given reaction (i.e., the degree of homology necessary for successful hybridization) will largely depend on the washing conditions to which the filter from the Southern blot is subjected after hybridization. "Low-stringency" conditions as defined herein will comprise washing a filter from a Southern blot with a solution of 0.2×SSC/0.1% SDS at 20° C. for 15 minutes. Standard-stringency conditions comprise a further washing step comprising washing the filter from the Southern blot a second time with a solution of 0.2×SSC/0.1% SDS at 37° C. for 30 minutes.

In a preferred embodiment according to this aspect of the invention, degenerate primers are prepared corresponding to one or more of the above peptides. The primers are combined with a genomic DNA from a target organism (i.e., the organism in which the EGIII-like cellulase is sought) under conditions suitable to initiate a standard PCR reaction. In this embodiment, it is advantageous to select degenerate primers corresponding to peptides (a) and/or (d) plus primers corresponding to (c) and/or (e) and amplify DNA with those primers. After the PCR reaction has been performed, the resulting DNA is run on a polyacrylamide gel and bands corresponding in size to the EGIII fragment comprising peptides (a) and/or (d) in addition to (c) and/or (e), i.e., those in the 400–1000 base pair range, are selected. These fragments are pooled and reamplified using primers corresponding to peptides (a) and/or (d) plus primers corresponding to peptide (b) or, alternatively, using primers corresponding to peptide (c) and/or (e) plus primers corresponding to peptide (b). Strong bands of the expected size (in the case of EGIII-like cellulases, the bands will correspond to approximately 250–500 base pair) are excised and sequenced. The isolated sequences are then used to design primers and these primers are used via, e.g., rapid amplification of genomic DNA ends (RAGE), to obtain the full length gene, see e.g., Mizobuchi, et al., *BioTechniques* 15:215–216 (1993).

The DNA that hybridizes with the DNA primers outlined above and thus identified by this method a corresponding EGIII encoding gene may be isolated by routine methods and used to express the corresponding EGIII-like cellulase according to routine techniques. Upon obtaining the cloned gene, routine methods for insertion of the DNA into a vector that can then be transformed into a suitable host cell are used. Culturing the transformed host cell under appropriate conditions results in production of the EGIII-like cellulase that can be obtained, purified and prepared as necessary for a particular application.

The EGIII-like cellulases of the invention are preferably isolated or purified. In the context of the present invention, purification or isolation generally means that the EGIII-like cellulase is altered from its natural state by virtue of separating the EGIII-like cellulase from some or all of the naturally occurring substituents with which it is associated in nature, e.g., the source organism or other cellulases or enzymes expressed by the source organism in conjunction with the EGIII cellulase. Similarly, the EGIII-like cellulases of the invention may be combined with other components that are not naturally present in the natural state. Isolation or purification may be accomplished by art recognized separation techniques such as ion exchange chromatography, affinity chromatography, hydrophobic separation, dialysis, protease treatment, ammonium sulfate precipitation or other protein salt precipitation techniques, centrifugation, size exclusion chromatography, filtration, microfiltration, gel electrophoresis or separation on a gradient to remove whole cells, cell debris, impurities, extraneous proteins, or enzymes undesired in the final composition.

A residue in an EGII-like cellulase which is "corresponding" or "equivalent" to a residue present in EGIII means a residue which exists in an equivalent position to that in EGIII, as indicated by primary sequence homology, tertiary structural homology (as shown by, e.g., crystal structure or computer modeling) or functional equivalence. A variant EGIII-like cellulase has an amino acid sequence that is derived from the amino acid sequence of a precursor EGIII-like cellulase. The precursor cellulases include naturally occurring cellulases and recombinant cellulases (as defined herein). The amino acid sequence of the EGIII-like cellulase variant is derived from the precursor EGII-like cellulase amino acid sequence by the substitution, deletion or insertion of one or more amino acids of the precursor amino acid sequence. Such modification is of the precursor DNA sequence that encodes the amino acid sequence of the precursor cellulase rather than manipulation of the precursor cellulase enzyme per se. Suitable methods for such manipulation of the precursor DNA sequence include methods disclosed herein and in commonly owned U.S. Pat. Nos. 4,760,025 and 5,185,258. Specific residues corresponding to the positions that are responsible for instability in the presence of surfactant are identified herein for substitution or deletion. The amino acid position number (e.g., +35) refers to the number assigned to the mature *Trichoderma reesei* EGIII sequence presented in FIG. 1. The invention is directed to the mutation of EGIII-like cellulases that contain amino acid residues at positions that are equivalent to the particular identified residue in *Trichoderma reesei* EGIII. A residue (amino acid) of a precursor cellulase is equivalent to a residue of *Trichoderma reesei* EGIII if it is either homologous (i.e., corresponding in position in either primary or tertiary structure) or is functionally analogous to a specific residue or portion of that residue in *Trichoderma reesei* EGIII (i.e., having the same or similar functional capacity to combine, react, or interact chemically or structurally). As used herein, numbering is intended to correspond to that of the mature EGIII amino acid sequence as illustrated in FIG. 1.

Homologous proteins can also be determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 15:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of a cellulase and $T.$ $reesei$ EGIII (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the cellulase in question to the $T.$ $reesei$ EGIII. The best model is the crystallographic model giving the lowest R factor for experimental diffraction data at the highest resolution available.

$$R\ factor = \frac{\sum_{h} |Fo(h)| - |Fc(h)|}{\sum_{h} |Fo(h)|}$$

Equivalent residues which are functionally analogous to a specific residue of $T.$ $reesei$ EGIII are defined as those amino acids of a cellulase which may adopt a conformation such that they either alter, modify or contribute to protein structure, substrate binding or catalysis in a manner defined and attributed to a specific residue of the $T.$ $reesei$ EGIII. Further, they are those residues of the cellulase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of $T.$ $reesei$ EGIII. The crystal structure of $T.$ $reesei$ EGIII is presented The Protein Society, Fourteenth Symposium. San Diego, Calif. Aug. 5–9, 2000, the disclosure of which is incorporated by reference in its entirety. The coordinates of CelB of *Streptomyces lividans*, a homologous member of the Family 12 glycosyl hydrolases is provided in Sulzenbacher, et al., *Biochemistry* 36:6032 (1997) and in Suizenbacher, et al., *Biochemistry* 38:4826 (1999).

"Variant" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of an enzyme variant is preferably achieved by modifying a DNA sequence which encodes for the native protein, transformation of that DNA sequence into a suitable host, and expression of the modified DNA sequence to form the derivative enzyme. The variant EGIII-like enzyme of the invention includes peptides comprising altered amino acid sequences in comparison with a precursor enzyme amino acid sequence wherein the variant EGIII-like enzyme retains the characteristic cellulolytic nature of the precursor enzyme but which may have altered properties in some specific aspect. For example, a variant EGIII-like enzyme may have an increased pH optimum or increased temperature or oxidative stability but will retain its characteristic cellulolytic activity. It is contemplated that the variants according to the present invention may be derived from a DNA fragment encoding a cellulase variant EGIII-like enzyme wherein the functional activity of the expressed cellulase derivative is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained.

"Cellulose containing fabric" means any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g., lyocell). Specifically included within the definition of cellulose containing fabric is any yarn or fiber made of such materials. Cellulose containing materials are often incorporated into blends with materials such as synthetic fibers and natural non-cellulosic fibers such as wool and silk.

"Cotton-containing fabric" means sewn or unsewn fabrics, yarns or fibers made of pure cotton or cotton blends including cotton woven fabrics, cotton knits, cotton denims, cotton yarns, raw cotton and the like. When cotton blends are employed, the amount of cotton in the fabric is preferably at least about 35 percent by weight cotton. When employed as blends, the companion material employed in the fabric can include one or more non-cotton fibers including cellulosic or synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Stonewashing composition" means a formulation for use in stonewashing cellulose containing fabrics. Stonewashing compositions are used to modify cellulose-containing fabrics prior to presentation for consumer sale, i.e., during the manufacturing process. In contrast, detergent compositions are intended for the cleaning of soiled garments.

"Stonewashing" means the treatment of cellulose containing fabric with a cellulase solution under agitating and cascading conditions, i.e., in a rotary drum washing machine, to impart a "stonewashed" appearance to the denim. The cellulase solution according to the instant invention will functionally replace the use of stones in such art-recognized methods, either completely or partially. Methods for imparting a stonewashed appearance to denim are described in U.S. Pat. No. 4,832,864, incorporated herein by reference in its entirety. Traditionally, stonewashing techniques have been applied to indigo dyed cotton denim.

"Detergent composition" means a mixture that is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers. Such compositions are generally used for cleaning soiled garments and are not used during the manufacturing process, in contrast to stonewashing compositions. Detergent compositions comprising cellulase are described in, for example, U.S. Pat. No. 5,290,474 and EP Publication No. 271 004, incorporated herein by reference.

"Expression vector" means a DNA construct comprising a DNA sequence that is operably linked to a suitable control sequence capable of effecting the expression of the DNA in a suitable host. Such control sequences may include a promoter to effect transcription, an optional operator sequence to control transcription, a sequence encoding suitable ribosome-binding sites on the mRNA, and sequences that control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* is cbhI. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors that serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook. Often, such expression vectors including the DNA sequences of the invention are transformed into a unicellular host by direct insertion into the genome of a particular species through an integration event (see e.g., Bennett & Lasure, More Gene Manipulations in Fungi, Academic Press, San Diego, pp. 70–76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally prokaryotic or eukaryotic hosts, including any transformable microorganism in which expression can be achieved. Preferred host strains include, but are not limited to, *Bacillus subtilis, Escherichia coli, Trichoderma reesei, Saccharomyces cerevisiae* or *Aspergillus niger*. A most preferred host is *A. niger*. Host cells are transformed or transfected with vectors constructed using recombinant DNA techniques. Such transformed host cells are capable of both replicating vectors encoding the variant EGIII-like enzymes or expressing the desired peptide product.

"Signal sequence" means a sequence of amino acids bound to the N-terminal portion of a protein that facilitates the secretion of the mature form of the protein outside of the cell. This definition of a signal sequence is a functional one. The mature form of the extracellular protein lacks the signal sequence that is cleaved off during the secretion process.

"DNA vector" means a nucleotide sequence which comprises one or are DNA fragments or DNA variant fragments encoding an EGIII-like cellulase or variants described above which can be used, upon transformation into an appropriate host cell, to cause expression of the variant EGIII-like cellulase.

"Functionally attached to" means that a regulatory region, such as a promoter, terminator, secretion signal or enhancer region is attached to a structural gene and controls the expression of that gene.

The present invention relates to the expression, purification and/or isolation and use of variant EGIII-like cellulases. These enzymes are preferably prepared by recombinant methods utilizing the gene identified and isolated according to the methods described above. However, enzymes for use in the present invention may be obtained by other art-recognized means such as purification from natural isolates.

The microorganism to be transformed for the purpose of expressing an EGIII-like cellulase according to the present invention may advantageously comprise a strain derived from *Trichoderma reesei* sp. Thus, a preferred mode for preparing EGIII-like cellulases according to the present invention comprises transforming a Trichoderma sp. host cell with a DNA construct comprising at least a fragment of DNA encoding a portion or all of the EGIII-like cellulase detected as described above. The DNA construct will generally be functionally attached to a promoter. The transformed host cell is then grown under conditions so as to express the desired protein. Subsequently, the desired protein product is purified to substantial homogeneity.

However, in a most preferred embodiment, the best expression vehicle for a given DNA encoding a variant EGIII-like cellulase is *Aspergillus niger*. See, WO 98/31821, the disclosure of which is incorporated by reference in its entirety, for a description of transformation into *A. niger*.

In one embodiment, the strain comprises *T. reesei* (*reesei*), a useful strain for obtaining overexpressed protein. For example, RL-P37, described by Sheir-Neiss, et al., *Appl. Microbiol. Biotechnol.* 20:46–53 is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing EGIII-like cellulases.

Where it is desired to obtain the EGIII-like cellulase in the absence of potentially detrimental native cellulolytic activity, it is useful to obtain a Trichoderma host cell strain which has had one or more cellulase genes deleted prior to introduction of a DNA construct or plasmid containing the DNA fragment encoding the EGIII-like cellulase. Such strains may be prepared by the method disclosed in U.S. Pat. No. 5,246,853 and WO 92/06209, which are hereby incorporated by reference. By expressing an EGIII-like cellulase in a host microorganism that is missing one or more cellulase genes, the identification and subsequent purification procedures are simplified. Any gene from Trichoderma sp.

which has been cloned can be deleted, for example, the cbh1, cbh2, egl1, and egl3 genes as well as those encoding EGIII and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with Trichoderma sp., the selectable marker is chosen so that the presence of the selectable marker in the transformants will not significantly affect the properties of the fungus. Such a selectable marker may be a gene that encodes an assayable product. For example, a functional copy of a Trichoderma sp. gene may be used which if lacking in the host strain results in the host strain displaying an auxotrophic phenotype.

In a preferred embodiment, apyr4⁻ derivative strain of Trichoderma sp. is transformed with a functional pyr4 gene, which thus provides a selectable marker for transformation. A pyr4⁻ derivative strain may be obtained by selection of Trichoderma sp. strains that are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4⁻ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, *Curr. Genet.* 9:359–365 (1991)). Selection of derivative strains is easily performed using the FOA resistance technique referred to above, and thus, the pyr4 gene is preferably employed as a selectable marker.

To transform pyr4⁻ Trichoderma sp. so as to be lacking in the ability to express one or more cellulase genes, a single DNA fragment comprising a disrupted or deleted cellulase gene is then isolated from the deletion plasmid and used to transform an appropriate pyr⁻ Trichoderma host. Transformants are then identified and selected based on their ability to express the pyr4 gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the pyr4 selectable markers.

Although the specific plasmid vectors described above relate to preparation of pyr⁻ transformants, the present invention is not limited to these vectors. Various genes can be deleted and replaced in the Trichoderma sp. strain using the above techniques. In addition, any available selectable markers can be used, as discussed above. In fact, any Trichoderma sp. gene that has been cloned, and thus identified, can be deleted from the genome using the above-described strategy.

As stated above, the host strains used are derivatives of Trichoderma sp. that lack or have a nonfunctional gene or genes corresponding to the selectable marker chosen. For example, if the selectable marker of pyr4 is chosen, then a specific pyr4⁻ derivative strain is used as a recipient in the transformation procedure. Similarly, selectable markers comprising Trichoderma sp. genes equivalent to the *Aspergillus nidulans* genes amdS, argB, trpC, niaD may be used. The corresponding recipient strain must therefore be a derivative strain such as argB⁻, trpC⁻, niaD⁻, respectively.

DNA encoding the EGIII-like cellulase is then prepared for insertion into an appropriate microorganism. According to the present invention, DNA encoding an EGIII-like cellulase comprises the DNA necessary to encode for a protein that has functional cellulolytic activity. The DNA fragment or DNA variant fragment encoding the EGIII-like cellulase or derivative may be functionally attached to a fungal promoter sequence, for example, the promoter of the cbh1 or egl1 gene.

It is also contemplated that more than one copy of DNA encoding a EGIII-like cellulase may be recombined into the strain to facilitate overexpression. The DNA encoding the EGIII-like cellulase may be prepared by the construction of an expression vector carrying the DNA encoding the cellulase. The expression vector carrying the inserted DNA fragment encoding the EGIII-like cellulase may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences. For example, pTEX is such a general-purpose expression vector. Genes or part thereof can be inserted downstream of the strong cbh1 promoter.

In the vector, the DNA sequence encoding the EGIII-like cellulase of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. The signal peptide provides for extracellular production of the EGIII-like cellulase or derivatives thereof. The DNA encoding the signal sequence is preferably that which is naturally associated with the gene to be expressed, however the signal sequence from any suitable source, for example an exo-cellobiohydrolase or endoglucanase from Trichoderma, is contemplated in the present invention.

The procedures used to ligate the DNA sequences coding for the EGIII-like cellulase of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account the permeability of the cell wall to DNA in Trichoderma sp. is very low. Accordingly, uptake of the desired DNA sequence, gene or gene fragment is at best minimal. There are a number of methods to increase the permeability of the Trichoderma sp. cell wall in the derivative strain (i.e., lacking a functional gene corresponding to the used selectable marker) prior to the transformation process.

The preferred method in the present invention to prepare Trichoderma sp. for transformation involves the preparation of protoplasts from fungal mycelium. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host Trichoderma sp. strain is dependent upon the calcium ion concentration. Generally, between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the Trichoderma sp. strain and the plasmid DNA is transferred to the nucleus. This fusion frequently leaves multiple copies of the plasmid DNA tenderly integrated into the host chromosome.

Usually a suspension containing the Trichoderma sp. protoplasts or cells that have been subjected to a permeability treatment at a density of $10^8$ to $10^9$/ml, preferably $2 \times 10^8$/ml are used in transformation. A volume of 100 microliters of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if $Pyr^+$ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may be made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the EGIII-like cellulases or derivatives thereof are recovered in active form from the host cell after growth in liquid media either as a result of the appropriate post translational processing of the novel EGIII-like cellulase or derivatives thereof.

The expressed EGIII-like cellulase may be recovered from the medium by conventional techniques including separations of the cells from the medium by centrifugation, filtration, and precipitation of the proteins in the supernatant or filtrate with a salt, for example, ammonium sulphate. Additionally, chromatography procedures such as ion exchange chromatography or affinity chromatography may be used. Antibodies (polyclonal or monoclonal) may be raised against the natural purified EGIII-like cellulase, or synthetic peptides may be prepared from portions of the EGIII-like cellulase molecule and used to raise polyclonal antibodies.

Although it is preferred that substitutions of residues from thermally more stable EG III-like cellulases into EG III cellulase result in more stable EG III, that is not the only possible useful outcome. To one of skill, it will be apparent that substitutions that result in less stable EG III cellulases are also useful in, e.g., compositions used to treat delicate textiles and in other applications where the prolonged existence of active EG III is not desired. In addition, one of skill will readily appreciate that converse substitutions are useful. For example, residues from less thermally stable EG III can be substituted into more stable EG III like cellulases to make less (or more) stable EG III homologs. Again, less stable homologs can be used when the prolonged presence of active cellulase is not required.

Treatment of textiles according to the present invention contemplates textile processing or cleaning with a composition comprising a cellulase. Such treating includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead" cotton, from cellulosic fabric or fibers. Immature cotton is significantly more amorphous than mature cotton and results in a lesser quality fabric when present due to, for example, uneven dyeing. The composition contemplated in the present invention further includes a cellulase component for use in washing of a soiled manufactured cellulose containing fabric. For example, the cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulase is known to increase the value of animal feed, improve the drainability of wood pulp, enhance food products and reduce fiber in grain during the grain wet milling process or dry milling process.

Treating, according to the instant invention, comprises preparing an aqueous solution that contains an effective amount of cellulase together with other optional ingredients including, for example, a buffer, a surfactant, and/or a scouring agent. An effective amount of cellulase enzyme composition is a concentration of cellulase enzyme sufficient for its intended purpose. Thus, for example, an "effective amount" of cellulase in a stonewashing composition according to the present invention is that amount which will provide the desired effect, e.g., to produce a worn and faded look in the seams and on fabric panels. Similarly, an "effective amount" of cellulase in a composition intended for improving the feel and/or appearance of a cellulose containing fabric is that amount which will produce measurable improvements in the feel, e.g., improving the smoothness of the fabric, or appearance, e.g., removing pills and fibrils which tend to reduce the sharpness in appearance of a fabric. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be treated is added can be readily determined by the skilled artisan based on the above factors as well as the desired result. In stonewashing processes, it has generally been preferred that the cellulase be present in the aqueous treating solution in a concentration of from about 0.5 to 5,000 ppm and most preferably about 10 to 200 ppm total protein. In compositions for the improvement of feel and/or appearance of a cellulose containing fabric, it has generally been preferred that the cellulase be present in the aqueous treating solution in a concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity which, in turn, depends on the nature of the cellulase employed. The exact concentration of buffer employed will depend on several factors that the skilled artisan can readily take into account. For example, in a preferred embodiment, the buffer, as well as the buffer concentration, is selected so as to maintain the pH of the final cellulase solution within the pH range required for optimal cellulase activity. The determination of the optimal pH range of the cellulases of the invention can be ascertained according to well-known techniques. Suitable buffers at pH within the activity range of the cellulase are well known to those skilled in the art in the field.

In addition to cellulase and a buffer, the treating composition may optionally contain a surfactant. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated cellulase composition can be prepared for use in the methods described herein. Such concentrates contain concentrated amounts of the cellulase composition described above, buffer and surfactant, preferably in an aqueous solution. When so formulated, the cellulase concentrate can readily be diluted with water so as to quickly and accurately prepare cellulase preparations having the requisite concentration of each constituent. When aqueous concentrates are formulated, these concentrates can be diluted so as to arrive at the requisite concentration of the components in the cellulase solution as indicated above. As is readily apparent, such cellulase concentrates will permit facile formulation of the cellulase solutions as well as permit feasible transportation of the composition to the location where it will be used. The treating concentrate can be in any art recognized form, for example, liquid, emulsion, gel, or paste. Such forms are well known to those skilled in the art.

When a solid cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283, which is incorporated herein by reference in its entirety.

Other materials can also be used with or placed in the cellulase composition of the present invention as desired, including stones, pumice, fillers, solvents, enzyme activators, and anti-redeposition agents depending on the eventual use of the composition.

By way of example, stonewashing methods will be described in detail, however, the parameters described are readily modified by the skilled artisan for other applications, e.g., improving the feel and/or appearance of a fabric. The cellulose containing fabric is contacted with the cellulase containing stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature that allow the cellulase enzyme to react efficiently with cellulose containing fabric, in this case to produce the stonewashed effect. However, such conditions are readily ascertainable by one of skill in the art. The reaction conditions effective for the stonewashing compositions of the present invention are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., which conditions would also be expected to be suitable for the cellulase of the invention, the optimal temperature conditions should be ascertained according to well known techniques with respect to the specific cellulase used.

Reaction times are dependent on the specific conditions under which the stonewashing occurs. For example, pH, temperature and concentration of cellulase will all affect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose containing fabrics, for example, depilling, softening, anti-pilling, surface fiber removal, anti-graying and cleaning. Preferably, the cellulase in the detergent composition is employed in a concentration of from about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase-protecting agent. The granule can be formulated so as to contain materials to reduce the rate of dissolution of the granule into the wash medium. Such materials and granules are disclosed in U.S. Pat. No. 5,254,283, which is incorporated herein by reference in its entirety.

The detergent compositions of this invention employ a surface-active agent, e.g., a surfactant, including anionic, non-ionic and ampholytic surfactants well known for their use in detergent compositions. In addition to the cellulase composition and the surfactant(s), the detergent compositions of this invention can optionally contain one or more of the following components:

Hydrolases Except Cellulase

Suitable hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified protein. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Builders

A. Divalent Sequestering Agents

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or Inorganic Electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as potassium monopersulfate, sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects. Similarly, bleaching agents and bleach catalysts as described in EP 684 304 may be used.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, amorphous silicas, clay, calcium silicate (such as Micro-Cell of Johns Manville Co.), calcium carbonate and magnesium oxide.

Masking Agents for Factors Inhibiting the Cellulase Activity

The cellulase composition of this invention is deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

Cellobiose, glucose and gluconolactone act sometimes as inhibitors. It is preferred to avoid the co-presence of these saccharides with the cellulase as far as possible. In case the co-presence in unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-Activators

The activators may vary depending on the specific cellulase. In the presence of proteins, cobalt and its salts, magnesium and its salts, and calcium and its salts, potassium and its salts, sodium and its salts or monosaccharides such as mannose and xylose, many cellulases are activated and their deterging powers are improved remarkably.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

The solubilizers include, for example, lower alcohols such as ethanol, benzenesulfonate salts, lower alkylbenzene-sulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes, and the like can be used, if desired, with the detergent compositions of this invention. Such components are conventionally employed in amounts heretofore used in the art.

When a detergent base used in the present invention is in the form of a powder, it may be one that is prepared by any known preparation methods including a spray-drying method and a granulation method. The detergent base obtained particularly by the spray-drying method, agglomeration method, dry mixing method or non-tower route methods are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space.

After the spray-drying, perfumes, enzymes, bleaching agents, inorganic alkaline builders may be added. With a highly dense, granular detergent base obtained such as by the spray-drying-granulation or agglomeration method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose containing fabric, for example soiled fabrics, in industrial and household uses at temperatures, reaction times and liquor ratios conventionally employed in these environments. The incubation conditions, i.e., the conditions effective for treating cellulose containing fabrics with detergent compositions according to the present invention, will be readily ascertainable by those of skill in the art. Accordingly, the appropriate conditions effective for treatment with the present detergents will correspond to those using similar detergent compositions which include known cellulases.

Detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, i.e., diluent, buffers, other enzymes (proteases), and the like at their conventional concentrations.

It is contemplated that compositions comprising cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover and for depilling and antipilling (pilling prevention).

The use of the cellulase according to the invention may be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

Example 1

Preparation of Genomic DNA Encoding EGIII-Like Cellulases

Genomic DNA was prepared for several different microorganisms for the purpose of undertaking a PCR reaction to determine whether EGIII-like cellulases are encoded by the DNA of a particular organism.

Genomic DNA was obtained from *Acremonium brachypenium* deposit no. CBS 866.73; *Chaetomium brasillience* deposit no. CBS 140.50; *Chaetomium vitellium* deposit no. CBS 250.85; *Emericella desertoru* deposit no. CBS 653.73; *Fusarium equiseti* deposit no. CBS 185.34; *Gliocladium roseum* deposit no. CBS 443.65; *Humicola grisea* var. *thermoidia* deposit no. CBS 225.63; *Myceliopthora thermophila* deposit no. ATCC 48102–48104; *Penicillium notatum* deposit no. ATCC 9178, 9179; and *Phanerochaete chrysosporium* deposit no. ATCC 28326 and isolated according to standard methods.

PCR was performed on a standard PCR machine such as the PCT-150 MicroCycler from MJ Research Inc. under the following conditions:

1) 1 minute at 98° C. for 1 cycle;
2) 1 minute at 94° C., 90 seconds at 40° C., 1 minute at 72° C.
3) repeat step 2 for 30 cycles,
4) 7 minutes at 72° C. for 1 cycle, and
5) lower temperature to 15° C. for storage and further analysis.

The following DNA primers were constructed for use in amplification of EGIII-like genes from the libraries constructed from the various microorganisms. All symbols used herein for protein and DNA sequences correspond to IUPAC IUB Biochemical Nomenclature Commission codes.

BOX1: primers coding for (N/Q)NLWG

| | |
|---|---|
| forward primer | FRG001: AAY AAY YTN TGG GG |
| forward primer | FRG002: CAR AAY YTN TGG GG |

BOX1': primers coding for NNN(F/L/Y/I/L/N/K)WG

| | |
|---|---|
| forward primer | FRG010: AAY AAY AAY HWI TGG GG |

BOX2: primers coding for ELMIW

| | |
|---|---|
| forward primer | FRG003: GAR YTN ATG ATH TGG |
| reversed primer | FRG004: CCA DAT CAT NAR YTC |

BOX2': primers coding for YELMIW

| | |
|---|---|
| forward primer | FRG011: TAY GAR YTI ATG ATH TGG |
| reversed primer | FRG012: CCA DAT CAT IAR YTC RTA |

BOX3: primers coding for GTE(P/C)FT

| | |
|---|---|
| reversed primer | FRG005: GTR AAN GGY TCR GTR CC |
| reversed primer | FRG006: GTR AAN GGY TCR GTY CC |
| reversed primer | FRG007: GTR AAN GGY TCY GTR CC |
| reversed primer | FRG008: GTR AAN GGY TCY GTY CC |
| reversed primer | FRG009: GTR AAR CAY TCN GTN CC |

PCR conditions were as follows: 10 μL of 10×reaction buffer (10×reaction buffer comprising 100 mM Tris HCl, pH 8–8.5; 250 mM KCl; 50 mM $(NH_4)_2SO_4$; 20 mM $MgSO_4$); 0.2 mM each of dATP, dTTP, dGTP, dCTP (final concentration), 1 μL of 100 ng/μL genomic DNA, 1 μL of PWO polymerase (Boehringer Mannheim, Cat# 1644–947) at 1 unit per μL, 500 mM primers (final concentration) and water to 100 μL. The solution was overlaid with mineral oil.

The PCR strategy was as follows: forward primers for BOX1 and BOX1' were combined with reversed primers from BOX3 in a mixture with the desired genomic DNA sample and run on a gel to obtain fragments in the 400–1000 base pair range. The fragments so obtained were pooled and the pool split into two approximately equal portions. The first pool was combined with the forward primers from BOX1 and BOX1' along with the reversed primer from BOX2. The second pool was combined with the forward primer from BOX2 along with the reversed primers from BOX3. Fragments having the approximate size relative to an EGIII-like cellulase considering the location of the primers within the gene, in this case corresponding to those between 250–500 base pairs, were isolated and sequenced.

From the sequenced fragments, it was possible to use the RAGE technique (rapid amplification of genomic ends) to rapidly obtain the sequence of the full length gene. Full length genes have been obtained and are provided with several additional EGIII-like cellulase sequences in FIG. 3. As shown in FIG. 3, full length genes isolated from *Hypocrea schweinitzii*, *Aspergillus aculeatus*, *Aspergillus kawachii* (1), *Aspergillus kawachii* (2), *Aspergillus oryzae*, *Humicola grisea*, *Humicola insolens*, *Chaetomium brasilliense*, *Fusarium equiseti*, *Fusarium javanicum* (1), *Fusarium javanicum* (2), *Gliocladium roseum* (1), *Gliocladium roseum* (2), *Gliocladium roseum* (3), *Gliogladium roseum* (4), *Memnoniella echinata*, Actinomycete 11AG8, *Streptomyces lividans* CelB, *Rhodothermus marinus*, *Emericella desertoru*, and *Erwinia carotovara* all comprised significant homology to EGIII from *Trichoderma reesei*.

Example 2

Temperature Stability Testing of EGIII and EGIII Like Cellulases

EGIII and EGIII homologs derived from *Humicola grisei*, *Humicola insolens*, *Emercella desertoru*, *Fusarium javanicum* and *Memnonella echinata* were tested to determine their stability under temperature stress.

Stability was assayed by following the rate of loss of activity upon incubation at a fixed, high temperature: Solutions of EGIII and EGIII-like cellulases at between 0.1 mg/ml and 0.5 mg/ml in 50 mM citrate/phosphate buffer at pH8.0 were incubated in a water bath at 48° C. At measured times 100 µl aliquots were removed and cooled (or frozen) rapidly. The remaining activity in these aliquots was assayed as detailed below. An irreversible thermal inactivation curve was generated by plotting remaining activity vs time, and the data fitted to a single exponential decay. The half-time of this exponential decay was determined as a measure of thermal stability.

The activity assay was performed as follows: In a well of a 96-well micro-titer plate, 10 µL of enzyme sample was added to 120 µL of substrate (4.2 mg/ml o-nitrophenyl cellobioside) in 50 mM potassium phosphate, pH 6.7. The plate was then incubated for 10 min at 40° C., and the reactions quenched with 70 µL of 0.2M glycine. The absorption at 410 nm (due to the o-nitrophenol released upon enzymatic cleavage of the substrate) was measured in a micro-titer plate reader. This end-point 410 nm reading was proportional to the cellulase activity in the nzyme sample.

The results of the stability testing were as shown in Table 1:

TABLE 1

| EG III LIKE ENZYME | HALF LIFE (MINUTES) |
| --- | --- |
| H. grisea | stable* |
| H. insolens | stable* |
| E. desertoru | 200 |
| F. javanicum | 93 |
| M. echinata | 192 |
| T. reesei (EGIII) | 23 |

*"stable" indicates less than 20% loss in activity in 200 mins.

As can be seen by the above results, the EGIII-like cellulases had significantly improved stability despite being relatively homologous to EGIII from *T. reesei*. Accordingly, it is apparent the residues that are different in the more stable homologs are critical for the improved stability of the EGIII-like cellulases and, as such, further improvement of the EGIII-like cellulases and EGIII itself by modifying these residues will result in additional improvements in the stability of EGIII and the EGIII-like enzymes.

Example 3

Stability of EGIII with Residues from Thermally Stable EGIII-like Cellulases

The following primers were used to produce cysteine substitutions in EGIII from *T. reesei* and in the EGIII-like cellulase from *H. grisea*. PCR was performed according to well-known techniques.

TABLE 2

PCR primers

| Variant | Forward primer | Reverse Primer |
| --- | --- | --- |
| W7Y | GCT GTG ACC AGT ACG CAA CCT TCA C | GTG AAG GTT GCG TAC TGG TCA CAG C |
| G31Q | GCT CTG GAT TTC AGT GCG TGA CGG | CCG TCA CGC ACT GAA ATC CAG AGC |
| A35V | GCT GCG TGA CGG TGG TAT CGC TCA GC | GCT GAG CGA TAC CAC CGT CAC GCA GC |
| T145E/ Y147W | CCA GAG CTG GGA GCT CTG GTA TGG CTA CAA CGG | CCG TTG TAG CCA TAC CAG AGC TCC CAG CTC TGG |
| Q162P | CCT TTG TGG CCC CGA CCA ACA CTA CC | GGT AGT GTT GGT CGG GGC CAC AAA GG |
| Y168F | CAC TAC CAA CTT CAG CGG AGA TGT C | GAC ATC TCC GCT GAA GTT GGT AGT G |

Briefly, DNA that encodes *T. reesei* EG III was amplified from a cDNA clone (Ward, et al., *Proc. of the Tricel Symposium on "Trichoderma reesei cellulases and other hydrolases"* Espoo, Finland 1993 Ed. Suominen, P. and Reinikanen, T. Foundation for Biotechnical and Industrial Research. 8, pp153–158.; and U.S. Pat. No. 5,475,101) using PCR primers that introduced a Bgl II restriction endonuclease site at the 5' end of the egl3 gene (immediately upstream of the first ATG codon) and an Xba I site at the 3' end (immediately downstream of the "stop" codon). The amplified fragment was then digested with Bgl II and Xba I, and ligated into pUC19 digested with Bgl II and Xba I.

Variants were made in this plasmid using the QuikChange™ mutagenesis methods (Stratagene). The variant genes were then subcloned into the Aspergillus expression vector pGAPT-pyrG. This is a variant of PGPT-pyrG (Berka and Barnett, *Biotech.Adv.* 7:127 (1989)) in which non-essential DNA has been excised. Vectors carrying the variant genes were then transformed into *A. niger* var. *awamori* and the resultant strains grown in shake-flask cultures (WO 98/31821).

EG III variants were then purified from cell-free supernatants of these cultures by column chromatography. Briefly, approximately 1 mL of Pharmacia Butyl Sepharose (Fast Flow) resin per 10 mg of EGIII was loaded into a disposable drip column with 0.5 M. ammonium sulfate. The column was then equilibrated with 0.05 M Bis Tris Propane and 0.05 M ammoniaum acetate at pH 8.

The EGIII-like cellulase containing supernatants were treated overnight with 0.18 mg/mL of endoglucanase H at 37° C. Ammonium sulfate was added to the treated supernatants to a final concentration of approximately 0.5 M. After centrifugation, the supernatant was loaded onto the column. The column was then washed with 3 volumes equilibration buffer and then eluted with 2×1 volumes of 0.05 M Bis Tris Propane and 0.05 M ammonium acetate, pH 8. Each volume of flow through was collected as a separate fraction with the EGIII-like cellulase appearing in the second fraction.

Equilibrium CD experiments were performed on an Aviv 62DS or 62ADS spectrophotometer, equipped with a 5 position thermoelectric cell holder supplied by Aviv. Buffer conditions were 50 mM bis-tris propane and 50 mM ammonium acetate adjusted to pH 8.0 with acetic acid. The final protein concentration for each experiment was in the range of 5–30 mM. Data was collected in a 0.1 cm path length cell.

Spectra were collected from 265~210 nm. Thermal denaturations were performed at 217 nm from 30 to 90° C. with data collected every two degrees. The equilibration time at each temperature was 0.1 minutes and data was collected for 4 seconds per sample.

The remainder of the pH 8.0 sample was divided into 5×400 μL aliquots. Two samples were adjusted to pH 5 and 7 with acetic acid and two others were adjusted to pH 9 and 10 with sodium hydroxide. Thermal denaturations of all five samples were performed simultaneously as described above. The melting points were determined according to the methods of Luo, et al., *Biochemistry* 34:10669 and Gloss, et al., *Biochemistry* 36:5612.

TABLE 3

Thermal Stability of Variant EGIII-like cellulases

| EG III Residue Substitution | Δ Tm | Tm ° C. | Fit error | Ave. Tm (std. dev.) | Ave. Fit error (std. dev.) |
|---|---|---|---|---|---|
| WT | 0.0 | 54.43 | | | |
| W7Y | −0.03 | 53.40 | | | |
| G31Q | −14.03 | 40.40 | 0.15 | | |
| A35V | | 61.60 | 0.24 | 61.83 (0.25) | 0.23 (0.14) |
| | 7.40 | 62.10 | 0.36 | | |
| | | 61.80 | 0.08 | | |
| T145E/Y147W | 0.77 | 55.20 | 0.05 | | |
| Q162P | 0.07 | 54.50 | 0.19 | | |
| Y168F | −0.03 | 54.40 | 0.12 | | |

As can be seen, recruiting the preferred residues from EGIII homologs into EGIII had a variety of effects. In one instance, changing the alanine at position 35 to a valine significantly increased the thermal stability of the enzyme. In another instance, changing the glycine at position 31 to a glutamine significantly decreased the thermal stability of the enzyme.

Example 4

Specific Activity of EGIII-like Cellulases

To assay for specific activity, a NPC hydrolysis assay was used. In a microtiter plate, 100 μl 50 mM sodium acetate, pH 5.5 and 20 μl 25 mg/mL o-NPC (o-Nitrophenyl o-D-Cellobioside (Sigma N 4764)) in assay buffer was added. The plate was incubated for 10 minutes at 40° C.

Once equilibrated, 10 μL EGIII-like cellulase was added and the plate incubated at 40° C. for another 10 minutes. To quench the hydrolysis and stop the reaction, 70 μL of 0.2 M glycine, pH 10.0 was added. The plate was then read in a microtiter plate reader at 410 nm. As a guide, 10 μL of a 0.1 mg/ml solution of *T. reesei* EGIII provided an OD of around 0.3.

The concentration of EGIII-like cellulase was determined by absorbance at 280 nm where the extinction coefficient was 78711 $M^{-1}$ $cm^{-1}$ or 3.352 $g/L^{-1}$ experimentally determined by the method of Edelhoch as described in Pace, et al., *Pro. Sci.* 4:2411 (1995).

TABLE 4

Specific Activity of EGIII-like Cellulases

| EGIII-like Cellulase | TM (° C.) | Specific Activity (relative to WT) |
|---|---|---|
| WT | 54.60 | 1.00 |
| W7Y | 53.4 | 1.09 |
| G31Q | 40.4 | 0.19 |
| A35V | 61.6 | 0.83 |
| T145E/Y147W | | 0.80 |
| | | 0.83 |
| Q162P | 54.5 | 0.99 |
| Y168F | 54.4 | 1.12 |

As can be seen from Table 4, the mutations that stabilize the EGIII-like cellulases derived from EGIII tend to retain activity. The change at position 31 to glutamine, which significantly decreased thermal stability also significantly decreased activity.

We claim:

1. A variant EGIII or EGIII-like cellulase, wherein said variant comprises a substitution or deletion at a position corresponding to one or more of residues selected from the group consisting of W7, A35, T145, Y147, and Q162 In EGIII from *Trichoderma reesei*.

2. The variant of claim 1, wherein said variant comprises a substitution at a position corresponding to one or more of residues selected from the group consisting o W7Y, A35V, T145E, Y147W, and Q162P in EGIII.

3. The cellulase according to claim 1, said cellulase being derived from a fungus, bacteria or Actinomycete.

4. The cellulase according to claim 3, wherein said cellulase is derived from a fungus.

5. The cellulase according to claim 4, wherein said fungus is a filamentous fuNgus.

6. The cellulase according to claim 5 wherein said filamentous fungus belongs to Euascomycete.

7. The cellulase according to claim 6 wherein said Euascomycete is Aspergillus spp., Gliocladium spp., Fusarium spp., Acremonium spp., Myceliophtora spp., Verticillium spp., Myrothecium spp., or Penicillium spp.

8. The cellulase according to claim 1, wherein said cellulase is an endoglucanase.

9. A DNA encoding the cellulase according to claim 1.

10. A vector comprising the DNA of claim 9.

11. A host cell transformed with the vector of claim 10.

12. A method of producing a cellulase comprising the steps of:
(a) culturing the host cell according to claim 11 in a suitable culture medium under suitable conditions to produce cellulase;
(b) obtaining said produced cellulase.

13. A detergent composition comprising a surfactant and a cellulase, wherein said cellulase comprises a variant EGIII-like cellulase comprising a substitution or deletion at a position corresponding to one or more of residues selected from the group consisting of W7, A35, T145, Y147, and Q162 in EGIII from *Trichoderma reesei*.

14. The detergent of claim 13, wherein said variant comprises a substitution at a position corresponding to one or more of residues residues selected from the group consisting of W7Y, A35V, T145E, Y147W and Q162P in EGIII.

15. The detergent according to claim 14, wherein said detergent is a laundry detergent.

16. The detergent according to claim 14, wherein said detergent is a dish detergent.

17. A method of treating a cellulase containing textile comprising contacting said textile with a variant EGIII or EGIII-like cellulase according to claim 1.

18. The method of claim 17 wherein the treatment is the stonewashing of indigo dyed denim.

19. A feed addItive comprising a EGIII or EGIII-like cellulase according to claim 1.

20. A method of treating wood pulp comprising contacting said wood pulp with a EGIII or EGIII-like cellulase according to claim 1.

21. A method of converting biomass to glucose comprising contacting said biomass with a EGIII or EGIII-like cellulase according to claim 1.

* * * * *